United States Patent [19]

Jaen et al.

[11] Patent Number: 4,678,787

[45] Date of Patent: Jul. 7, 1987

[54] 4H-1-BENZOPYRAN-4-ONES AND THEIR SULFUR CONTAINING ANALOGS

[75] Inventors: Juan C. Jaen, Plymouth; Lawrence D. Wise, Ann Arbor, both of Mich.

[73] Assignee: Warner-Lambert Company, Morris Plains, N.J.

[21] Appl. No.: 799,580

[22] Filed: Nov. 22, 1985

Related U.S. Application Data

[63] Continuation-in-part of Ser. No. 696,364, Jan. 30, 1985, abandoned.

[51] Int. Cl.$^4$ .................. A61K 31/495; C07D 405/14; C07D 409/14
[52] U.S. Cl. ..................................... 514/253; 514/318; 514/319; 514/333; 544/295; 544/357; 544/364; 544/376; 546/190; 546/256; 546/269
[58] Field of Search ............... 544/295, 357, 364, 376; 546/190, 256, 269; 514/253, 318, 319, 333

[56] References Cited

U.S. PATENT DOCUMENTS

| 3,098,854 | 7/1963 | Klosa et al. | 544/268 |
| 4,320,128 | 3/1982 | Fake | 544/360 |
| 4,428,955 | 1/1984 | Friebe et al. | 544/193 |

OTHER PUBLICATIONS

Witte, et al, "Chemical Abstracts", vol. 78, 1973, Col. 43520x.

*Primary Examiner*—Glennon H. Hollrah
*Assistant Examiner*—James H. Turnipseed
*Attorney, Agent, or Firm*—Joan Thierstein

[57] ABSTRACT

Novel 4H-1-benzopyran-4-ones and their sulfur containing analogs are disclosed which are efficacious for the treatment of psychosis including schizophrenia.

23 Claims, No Drawings

4H-1-BENZOPYRAN-4-ONES AND THEIR SULFUR CONTAINING ANALOGS

CROSS REFERENCE TO RELATED APPLICATION

This is a continuation-in-part of U.S. patent application Ser. No. 696,364 of Jan. 30, 1985, now abandoned.

BACKGROUND OF THE INVENTION

The present invention provides novel compounds, synthesis, pharmaceutical compositions and uses of the compounds, particularly as antipsychotic agents.

Numerous examples of aminoalkoxybenzopyranones are known. For example, in U.S. Pat. No. 4,428,955, Boehringer discloses compounds of general Formula III for use in the treatment of allergies. Compounds including those, generally, of Formula IV shown in U.S. Pat. No. 4,320,128 are for use as antihypertensives and in U.S. Pat. No. 3,098,854, Chem.-Pharm. Fabrik describes compounds of Formula V having use as vasodilators. However, none of the aminoalkoxybenzopyranones described in the noted U.S. Patents suggest the combinations of structural variations of the compounds of the present invention described hereinafter. Particularly, an antipsychotic use for the above disclosed compounds is not within the teachings of the patents noted. Copending U.S. application Ser. No. 651,972 filed Sept. 19, 1984, now abandoned discloses benzopyran-2-ones for antipsychotic use. The present invention of benzopyran-4-one derivatives is not suggested by such previously disclosed compounds.

SUMMARY OF THE INVENTION

The present invention is a compound of Formula I wherein X is oxygen or sulfur; R is A or B wherein$=$ is a single or double bond wherein Ar is (a) phenyl, (b) phenyl substituted by lower alkyl, lower alkoxy, lower thioalkoxy, halogen, or trifluoromethyl, or (c) Het wherein Het is 2-, 3-, or 4-pyridinyl or 2-, 3-, or 4-pyridinyl substituted by lower alkyl, lower alkoxy, or halogen; 2-, 4-, or 5-pyrimidinyl or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl or 2- or 3-thienyl substituted by lower alkyl or halogen; 2- or 3-furanyl or 2- or 3-furanyl substituted by lower alkyl or halogen; 2- or 5-thiazolyl or 2- or 5-thiazolyl substituted by lnower alkyl or halogen, and the $-O-(CH_2)_{2-5}-R$ group is at the 5, 6, 7, or 8 position of the compound, or a pharmaceutically acceptable acid addition salt thereof.

The novel compounds of Formula I are named as benzopyranones or benzothiopyranones by virtue of a fused ring system having a carbonyl group in the heterocyclic ring portion of the fused ring. The heterocyclic fused ring system is numbered counterclockwise starting with X as depicted in Formula VI. By virtue of the carbonyl group at the four position these compounds are called benzopyran-4-ones when X is oxygen and benzothiopyran-4-ones when X is sulfur.

Additionally, the present invention is a process for the preparation of a compound of Formula I as defined above which comprises reacting a compound of Formula II, wherein Hal is halogen and X is oxygen or sulfur with an amine having the Formula HA or HB wherein A or B is as defined above (see Scheme I).

Also the process of the present invention is the preparation of the compound of Formula II$_1$ which comprises reacting a compound of Formula VII with 1-bromo-3-halopropane or other appropriately substituted alkane in the presence of anhydrous $K_2CO_3$. The compounds of Formula II$_2$ can be prepared in a similar manner from a compound of Formula VIII (see Scheme II).

On the other hand, the process of the present invention includes the preparation of the compound of Formula II$_3$ which comprises: (1) reacting 2,6-dihydroxyacetophenone, 1-bromo-3-chloropropane or appropriately substituted alkane, and potassium carbonate to obtain a compound of Formula IX, then (2) treating the product of step 1 with sodium metal and ethyl formate, and finally (3) the product of step 2 is treated with HCl in ethanol to obtain the compound of Formula II$_3$ (see Scheme III).

The present invention is also a pharmaceutical composition comprising an amount effective for the treatment of psychosis, such as schizophrenia, of a compound of the Formula I defined above or a pharmaceutically acceptable acid addition salt thereof, in admixture with a pharmaceutically acceptable carrier.

Further, the present invention is a method of treating psychosis which comprises administering to humans, exhibiting psychotic symptoms, an effective amount of the compound I as defined above or a pharmaceutically acceptable salt thereof.

Antipsychotic activity is determined by standard laboratory means.

All compounds shown in the following Table 1 are active in laboratory tests that have been useful as predictors of antipsychotic efficacy (e.g., treatment of schizophrenia). Among these tests described by J. R. McLean, R. B. Parker, and L. L. Coughenour in *Pharmacol. Biochem. Behav.* 1978 (8) 97, is one which screens for compounds that decrease exploratory locomotor activity in mice and rats without causing ataxia. Table 1 shows the ED50 doses for inhibition of locomotor activity (Inh. Loc. Act.) (mouse, IP) and (rat, PO). All known antipsychotic agents are active in this test. Our compounds are also active at doses as low as 0.35 mg/kg.

Further study of these compounds indicates that their mechanism of action involves the selective activation of presynaptic dopamine receptors in the brain of animals. Thus, they show in vitro affinities for the dopamine receptor in the $10^{-6}$-$10^{-7}$ molar range, as measured by the inhibition of [$^3$H]haloperidol binding. (See: D. R. Burt, I. Creese, and S. H. Snyder, *Mol. Pharmacol.* 1976 (12) 800). Additional evidence for this mode of action includes the decrease of prolactin release in α-methyl-para-tyrosine-treated rats (observed with treatment using the compound of Formula I wherein X is oxygen; $-O-(CH_2)_3-R$ is in the 7 position of the fused ring system; and R is 4-(phenyl)piperazinyl), (see: A. G. Frantz; *Prog. Brain Res.* 1973 (39) 311) inhibition of the synthesis of dopamine in rats treated with gamma-butyrolactone (GBL) (see: J. R. Walters and R. H. Roth, *Naunyn-Schmiedeberg's Arch. Pharmacol.* 1976 (296) 5) (observed with treatment using compounds of Formula I wherein X is oxygen; $-O-(CH_2)_3$ R is in the 7 position; and R is 4-(phenyl)-1,2,5,6-tetrahydro pyridinyl or 4-(phenyl)piperazinyl) and the inhibition of dopamine neuron firing rate observed with treatment using the compound of Formula I wherein X is oxygen; $-O-(CH_2)_3-R$ is in the seven position and R is 4-(phenyl)piperazinyl in single unit recording experiments (see: L. R. Skirboll, A. A. Grace, and B. S. Bunney; *Science*, 1979 (206) 80). Because of this mechanism of action, it is believed that these compounds should have little or no tendency to produce the extrapyramidal side effects observed with classical neuroleptic drugs. Thus, the present invention provides antipsychotic agents such as for the treatment of schizophrenia having a low probability of side effects.

Analogs of compounds of Formula I were prepared and were found to be inactive in the McLean et al test described above. For example, an aminoalkoxybenzopyranone incorporating a dialkylaminopropoxy side was prepared as an example of the type of structure V, which is claimed by Chem.-Pharm. Fabrik (U.S. Pat. No. 3,098,854) noted above as vasodilator. Equally, an aminoalkoxybenzopyranone was prepared as an example of structure III, claimed by Boehringer (U.S. Pat. No. 4,428,955) for the treatment of allergies. In both instances, the structural features of these compounds are inappropriate for the desired dopaminergic activity.

These compounds are active in animal tests which are predictive of neuroleptic activity for the treatment of subjects exhibiting the symptoms of major psychoses such as schizophrenia. Regardless of the route of administration selected, the compounds of the present invention are formulated into pharmaceutically acceptable dosage forms by conventional methods known to the pharmaceutical art. In general a preferred method of administration is, however, by oral dosage forms.

The compounds can be administered in such unit oral dosage forms as tablets, capsules, pills, powders, or granules. They may also be administered rectally, vaginally in such forms as suppositories or bougies. They may also be introduced parenterally, (e.g., subcutaneously, intravenously, or intramuscularly), using forms known to the pharmaceutical art.

An effective but nontoxic quantity of the compound of Formula I or the salts thereof is employed in treatment. The dosage regimen for treating psychosis by the compounds of this invention is selected in accordance with a variety of factors including the type, age, weight, sex, and medical condition of the subject, the severity of the psychosis, the route of administration, and the particular compound employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

Initial dosages of the compounds of the invention are ordinarily in the area of 1 mg/kg up to at least 100 mg/kg per dose orally, preferably 1 to 50 mg/kg orally are given. Each dose is given from one to four times daily or as needed. When other forms of administration are employed equivalent doses are administered.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, cyclohexanesulfamates, methansulfonates, ethanesulfonates, benzenesulfonates, toluenesulfonates and the like. Additionally, the compounds of this invention may be administered in a suitable hydrated or solvent form.

The following Table 1 shows novel compounds of Formula I and their activity for use as described above.

TABLE 1

4H—1-Benzopyran-4-ones of Formula I, with Antipsychotic Activity

| Cpd. No. | X | —O—(CH$_2$)$_{2-5}$R Position on Ring | | Definition of R | Molecular Formula | MP | Inh. Loc. Act. (mouse IP) (ED$_{50}$); mg/kg | Inh. Loc. Act. (rat PO) (ED$_{50}$); mg/kg |
|---|---|---|---|---|---|---|---|---|
| 1 | 0 | —(CH$_2$)$_3$— | 7 | 4-phenyl-1,2,3,6-tetrahydro-1-pyridinyl | C$_{23}$H$_{23}$NO$_3$ | 134.0–135.5 | 0.7 | 29.5 |
| 2 | 0 | —(CH$_2$)$_3$— | 7 | 4-phenylpiperazinyl | C$_{22}$H$_{24}$N$_2$O$_3$(H$_2$O) | 149–152 | 2.4 | 4.3 |
| 3 | 0 | —(CH$_2$)$_3$— | 7 | 4-(4-chlorophenyl)-piperazinyl | C$_{22}$H$_{23}$ClN$_2$O$_3$·(H$_2$O) | 160–163 | 11.1 | 18.6 |
| 4 | 0 | —(CH$_2$)$_3$— | 7 | 4-(2,3-dimethylphenyl)-piperazinyl | C$_{24}$H$_{28}$N$_2$O$_3$·HBr (½ H$_2$O) | 255–257 | 11.2 | 13.2 |
| 5 | 0 | —(CH$_2$)$_3$— | 7 | 4-(3-chlorophenyl)-piperazinyl | C$_{22}$H$_{23}$ClN$_2$O$_3$·HCl (4 H$_2$O) | >275 | 7.7 | 8.5 |
| 6 | 0 | —(CH$_2$)$_3$— | 7 | 4-(2-methoxyphenyl)-piperazinyl | C$_{23}$H$_{26}$N$_2$O$_4$·HCl (½ H$_2$O) | 193–195 | 7.7 | >30 |
| 7 | 0 | —(CH$_2$)$_3$— | 7 | 4-phenylpiperidinyl | C$_{23}$H$_{25}$NO$_3$·HCl (H$_2$O) | 182–184 | 14.8 | >30 |
| 8 | 0 | —(CH$_2$)$_3$— | 7 | 4-(2-methylphenyl)-piperazinyl | C$_{23}$H$_{26}$N$_2$O$_3$·2 HBr | 243.0–244.5 | 2 | 30 |
| 9 | 0 | —(CH$_2$)$_3$— | 7 | 4-(3-methylphenyl)-piperazinyl | C$_{23}$H$_{26}$N$_2$O$_3$·2 HCl (½ H$_2$O) | 210–212 | 5.4 | 4.8 |
| 10 | 0 | —(CH$_2$)$_3$— | 7 | 4-(4-methylphenyl)-piperazinyl | C$_{23}$H$_{26}$N$_2$O$_3$·2 HCl (H$_2$O) | 211–213 | 6.1 | 22.3 |
| 11 | 0 | —(CH$_2$)$_3$— | 7 | 4-(4-fluorophenyl)-piperazinyl | C$_{22}$H$_{23}$FN$_2$O$_3$·2 HCl (H$_2$O) | 229–230 | 7 | 7.1 |
| 12 | 0 | —(CH$_2$)$_3$— | 7 | 4-(2-pyridyl)-piperazinyl | C$_{21}$H$_{23}$N$_3$O$_3$·2 HCl (H$_2$O) | 267–269 | 5–6 | 1.7 |
| 13 | 0 | —(CH$_2$)$_3$— | 7 | 4-(2-chlorophenyl)-piperazinyl | C$_{22}$H$_{23}$ClN$_2$O$_3$·1½ HCl (H$_2$O) | 201–203 | >30 | NA* |
| 14 | 0 | —(CH$_2$)$_3$— | 7 | 4-(3,4-dichlorophenyl)-piperazinyl | C$_{22}$H$_{22}$Cl$_2$N$_2$O$_3$·HCl | 258–259 | 14–15 | 17.8 |
| 15 | 0 | —(CH$_2$)$_3$— | 7 | 4-(4-methoxyphenyl)-piperazinyl | C$_{23}$H$_{26}$N$_2$O$_4$·HCl | 230–233 | 30 | >30 |
| 16 | 0 | —(CH$_2$)$_3$— | 7 | 4-(3-hydroxyphenyl)-piperazinyl | C$_{22}$H$_{24}$N$_2$O$_4$·HCl (½ H$_2$O) | 240–243 | >30 | NA* |

TABLE 1-continued

4H—1-Benzopyran-4-ones of Formula I, with Antipsychotic Activity

| Cpd. No. | X | —O—(CH$_2$)$_{2-5}$R | | Position on Ring | Definition of R | Molecular Formula | MP | Inh. Loc. Act. (mouse IP) (ED$_{50}$); mg/kg | Inh. Loc. Act. (rat PO) (ED$_{50}$); mg/kg |
|---|---|---|---|---|---|---|---|---|---|
| 17 | O | —(CH$_2$)$_3$— | | 7 | 4-(3,4-dimethyl-phenyl)piperazinyl | C$_{24}$H$_{28}$N$_2$O$_3$. 2 HCl (½ H$_2$O) | 238.0–238.5 | 3 | 7.3 |
| 18 | O | —(CH$_2$)$_3$— | | 5 | 4-(phenyl)piperazinyl | C$_{22}$H$_{24}$N$_2$O$_3$ | 106–112 | 13.3 | 15.6 |
| 19 | O | —(CH$_2$)$_4$— | | 6 | 4-(phenyl)piperazinyl | C$_{23}$H$_{26}$N$_2$O$_3$. 2 HCl (H$_2$O) | 193–195 | 3 | 1.5 |
| 20 | O | —(CH$_2$)$_4$— | | 7 | 4-(phenyl)piperazinyl | C$_{23}$H$_{26}$N$_2$O$_3$. 1½ HCl (H$_2$O) | 204–206 | 0.35 | 1.9 |
| 21 | O | —(CH$_2$)$_3$— | | 7 | 4-(2-pyrimidyl)piperazinyl | C$_{20}$H$_{22}$N$_4$O$_3$ (2CH$_3$OH) | 124–129 | 23.7 | >30 |

*NA means not available

Certain compounds within the scope of Formula I are preferred, since they have a more advantageous pharmacologic effect.

Thus, the compounds of the Formula I having the —O—(CH$_2$)$_{2-5}$—R in the 6- or 7-position of the ring system are preferred. More preferred are the compounds of Formula I wherein —O—(CH$_2$)$_{2-5}$—R is —O—(CH$_2$)$_3$ or $_4$—R and Ar is unsubstituted.

Among the most preferred are 7-[3-(4-phenyl-1,2,3,6-tetrahydro-1-pyridyl)propoxy]-4H-1-benzopyran-4-one, 7-[3-(4-phenylpiperazinyl)propoxy]-4H-1-benzopyran-4-one, 7-[3-(4-(2-pyridylpiperazinyl))propoxy)-4H-1-benzopyran-4-one, 6-[4-(4-phenyl-1-piperazinyl)-butoxy]-4H-1-benzopyran-4-one, and 7-[4-(4-phenyl-1-piperazinyl)butoxy]-4H-1-benzopyran-4-one.

Examples of —(CH$_2$)—$_{2-5}$ are ethylene, propylene, butylene, and pentylene.

Ar as used in the description of the present invention means (a) phenyl, (b) phenyl substituted, for example, by from one to three substituents such as alkyl of from one to six carbons, inclusive; alkoxy of from one to six carbons, inclusive; halogen; or (c) Het wherein Het is 2-, 3-, or 4-pyridinyl or 2-, 3-, or 4-pyridinyl substituted by alkyl of from one to six carbons, inclusive, alkoxy of from one to six carbons, inclusive, or halogen; 2-, 4-, or 5-pyrimidinyl or 2-, 4-, or 5-pyrimidinyl substituted by alkyl of from one to six carbons, inclusive, alkoxy of from one to six carbons, inclusive, or halogen; 2-pyrazinyl or 2-pyrazinyl substituted by alkyl of from one to six carbons, inclusive, alkoxy of from one to six carbons, inclusive or halogen; 2- or 3-thienyl or 2- or 3-thienyl substituted by alkyl of from one to six carbons, inclusive; 2- or 3-furanyl or 2- or 3-furanyl substituted by alkyl of from one to six carbons, inclusive, or halogen; or 2- or 5-thiazolyl or 2- or 5-thiazolyl substituted by alkyl of from one to six carbons, inclusive, or halogen.

Alkyl from one to six carbons, inclusive, means methyl, ethyl, propyl, butyl, pentyl, hexyl, and isomers thereof.

Alkoxy of from one to six carbons, inclusive, means methoxy, ethoxy, propoxy, butoxy, pentoxy, hexoxy, and isomers thereof.

Halogen includes particularly chloro, fluoro, trifluoromethyl, or bromo.

Generally, the compounds of the Formula I are prepared by reacting a mixture of a compound of Formula II defined above; e.g., (3-chloropropoxy)-4-H-benzopyran-4-one, which is prepared by a process as shown in Example 1 hereinafter, the appropriate compound of Formula HA or HB as defined above, in approximate equimolar amounts in the presence of NaHCO$_3$ and catalytic NaI and in a solvent such as dimethylformamide (DMF), acetonitrile, ethanol, or the like at a temperature of 50° to 120° C., preferably 85°–90° C. Separation and purification is accomplished by conventional methods, for example, the free base, in some cases, is purified by recrystallization of the crude product from ethyl acetate.

The synthesis of the intermediates of Formula II$_1$ is generally accomplished (see Scheme II) by contacting 7-hydroxy-4H-1-benzopyran-4-one with an appropriately substituted alkane such as 1-bromo-3-chloropropane in the presence of anhydrous alkali metal carbonate in a solvent such as acetone under reflux conditions for from 2 to 24 hours, preferably from 10 to 12 hours. Intermediates of Formula II$_2$ are prepared in a similar manner.

The intermediates of Formula II$_3$ are generally prepared (see Scheme III) from a mixture of 2,6-dihydroxyacetophenone, an appropriately substituted alkane such as 1-bromo-3-chloropropane in the presence of an alkali metal carbonate. Again, as in the preparation of II$_1$ described above the present mixture is refluxed in a solvent such as acetone for from two hours to several days preferably about 60 hours. The crude product of the reflux is further treated with sodium metal in ethyl formate, also under reflux conditions, for from 30 minutes to four hours, preferably for about an hour. The compounds of Formula II$_3$ may be obtained.

In each case, conventional methods of separation and purification are used.

The starting materials required for the processes described in this invention are either commercially available or can be synthesized by methods known in the art of organic chemistry. For example, the 6- or 7-hydroxy-4H-1-benzopyran-4-one can be prepared according to G. N. Dorafeenko, and V. V. Tkachenko, *Chem. Heterocyclic Compounds*, 1972 (8) 935.

The preparation for compounds of the Formula I wherein X is sulfur are likewise prepared by methods within the skill of the art, from starting materials either commercially available or synthesized by methods known in the art.

The acid addition salts of Formula I compounds are prepared by reacting the compound with the stoichometric equivalent of the acid corresponding to the pharmacologically acceptable acid addition salt, for example, the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

DESCRIPTION OF THE PREFERRED EMBODIMENTS

The following preparations and Examples will further illustrate the invention, without limiting it thereto.

PREPARATION 1

7-(3-Chloropropoxy)-4H-1-benzopyran-4-one

A mixture of 7-hydroxy-4H-1-benzopyran-4-one, VII (40.5 g; 0.25 mole; prepared according to G. N. Dorafeenko and V. V. Tkachenko, *Chem. Heterocyclic Compounds*, 1972 (8) 935), 1-bromo-3-chloropropane (78.5 g; 0.50 mole) and anhydrous potassium carbonate (49 g; 0.50 mole) in 1000 ml of acetone was heated at reflux for 16 hours. The mixture was filtered through celite and concentrated in vacuo. The thick red oil which remained was triturated with ether, upon which 57.8 g (97%) of the title compound was obtained, mp 72°–73° C.

EXAMPLE 1

7-[3-(4-(2-Chlorophenyl)-1-piperazinyl)propoxy]-4H-1-benzopyran-4-one

The following procedure is typical for the preparation of benzopyran-4-ones of general Formula I wherein X is oxygen.

A mixture of 7-(3-chloropropoxy)-4H-benzopyran-4-one as prepared above in Preparation I (2.38 g; 10 mmol), 1-(2-chlorophenyl)piperazine dihydrochloride (2.96 g; 11 mmol), sodium bicarbonate (3 g; 35 mmol), sodium iodide (0.1 g; 0.6 mmole) in 50 ml dimethylformamide was mechanically stirred and heated at 85°–90° C. for seven hours. The solvent was then evaporated in vacuo and the residue partitioned between water and dichloromethane. The organic phase was treated with an excess of 10% HCl solution in methanol, evaporated in vacuo and the residue recrystallized from ethanol/ethyl acetate to yield 3.2 g of 7-[3-(4-(2-chlorophenyl)-1-piperazinyl)propoxy]-4H-1-benzopyran-4-one as its hydrochloride salt, mp 201°–203° C. (dec).

All other 7-(3-aminopropoxy)-4H-1-benzopyran-4-ones that appear in Table 1 were prepared by this procedure. In some cases, the free base was purified by recrystallization of the crude product from ethyl acetate.

EXAMPLE 2

7-[3-(4-Phenyl-1,2,3,6-tetrahydro-1-pyridyl)propoxy]-4H-1-benzopyran-4-one

By a procedure similar to the one described above, the title compound was prepared as its hydrochloride salt, mp 128°–132° C. (dec).

EXAMPLE 3

7-[3-(4-Phenyl-1-piperidinyl)propoxy]-4H-1-benzopyran-4-one

By a procedure similar to the one described above, the title compound was prepared as its hydrochloride salt, mp 182°–184° C.

Additional examples of 4H-1-benzopyran-4-ones prepared include 5- and 6-substituted analogs within the compounds of Formula I wherein X is oxygen, as well as the product of replacement of the trimethylene chain of the compound in Example 1 above, by a tetramethylene chain. Such compounds are further shown in Table 1 above.

PREPARATION 2

7-(4-Chlorobutoxy)-4H-1-benzopyran-4-one

The title compound, mp 75°–78° C. was prepared as described above for 7-(3-chloropropoxy)-4H-1-benzopyran-4-one, starting from 1-bromo-4-chlorobutane and 7-hydroxy-4H-1-benzopyran-4-one.

EXAMPLE 4

7-[4-(4-Phenyl-1-piperazinyl)butoxy]-4H-1-benzopyran-4-one

The title compound was prepared by the method described above in Examples 1–3. Thus, 7-(4-chlorobutoxy)-4H-1-benzopyran-4-one, as prepared above in Preparation 2, (3.79 g, 15 mmol) was treated with 1-phenylpiperazine (2.59 g; 16 mmol) in the usual way, yielding 3.76 g of 7-[4-(4-phenyl-1-piperazinyl)-butoxy-]4H-1-benzopan-4-one.1.5 HCL (H$_2$O), mp 204°–206° C.

PREPARATION 3

6-(4-Chlorobutoxy)-4H-1-benzopyran-4-one

The title compound, mp 75°–77° C., was prepared by a procedure similar to that described for 7-(3-chloropropoxy)-4H-1-benzopyran-4-one above, starting with 1-bromo-4-chlorobutane and 6-hydroxy-4H-1-benzopyran-4-one (obtained by the method of Dorofeenko and Tkachenko, vide supra).

EXAMPLE 5

6-[4-(4-phenyl-1-piperazinyl)butoxy]-4H-1-benzopyran-4-one

The title compound was prepared by the method described above for the compounds of Formula I wherein X is oxygen. Thus, 6-(4-chlorobutoxy)-4H-1-benzopyran-4-one, as prepared above in Preparation 3, (3.79 g; 15 mmol) was reacted with 1-phenylpiperazine (2.59 g; 16 mmol) in the usual way, yielding 3.5 g of 6-[4-(4-phenyl-1-piperazinyl)butoxy]-4H-1-benzopyran-4-one as its dihydrochloride salt, mp 193°–195° C. (See Scheme I.)

PREPARATION 4

5-(3-Chloropropoxy)-4H-1-benzopyran-4-one 2,6-Dihydroxyacetophenone (20 g; 131 mmol), 1-bromo-3-chloropropane (31.48 g, 200 mmol), and potassium carbonate (14.7 g, 150 mmol) were refluxed in 500 ml acetone for 60 hours. The mixture was then filtered and evaporated in vacuo to give 28 g of crude 2-(3-chloropropoxy)-6-hydroxyacetophenone, which was used directly without further purification.

2-(3-Chloropropoxy)-6-hydroxyacetophenone, 5, (28 g; 120 mmol) was dissolved in 100 ml ethyl formate, treated with sodium metal (10.9 g, 474 mmol), and refluxed for one hour. The mixture was then poured over ice, the yellow solid formed was filtered and dried, and immediately refluxed with 2 ml concentrated HCl in 200 ml ethanol. After cooling, the acid was neutralized with anhydrous potassium carbonate and the solution filtered and concentrated. The residual red oil turned into a pasty solid upon cooling in the freezer, mp 50°–56° C., and was identified as the title compound (see Scheme III).

EXAMPLE 6
5-3-(4-phenyl-1-piperazinyl)propoxyl-4H-1-benzopyran-4-one
The title compound was prepared by the method described above for Examples 1 through 5 above. In this instance, the free base isolated, mp 106°–112° C.
FORMULAE
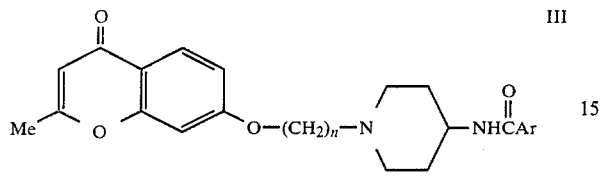
III
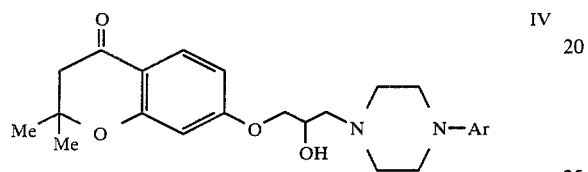
IV
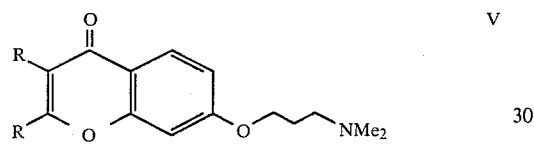
V
FORMULA
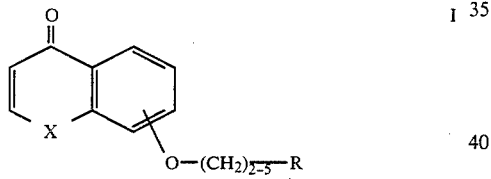
I
A
B
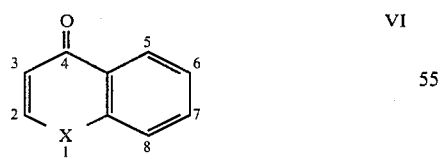
VI
SCHEME I
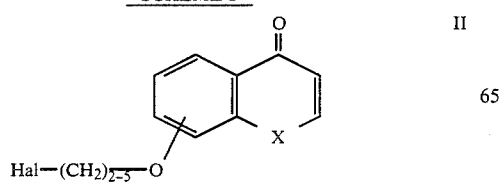
II
-continued
SCHEME I
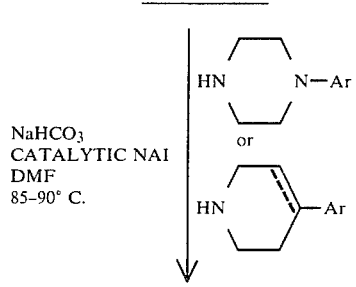
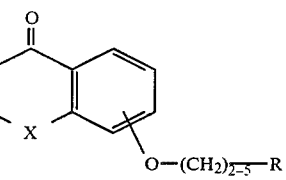
I
SCHEME II
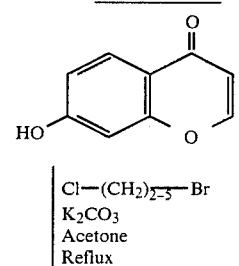
VII
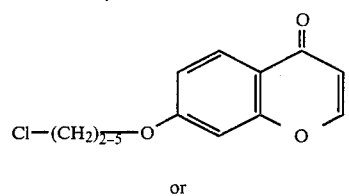
II$_1$
or
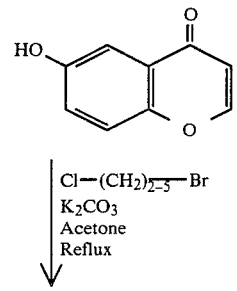
VIII
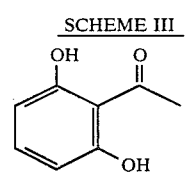
II$_2$
SCHEME III -continued
SCHEME III

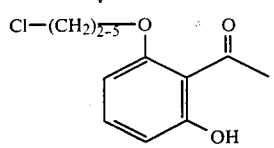

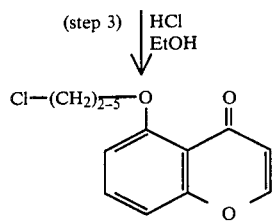

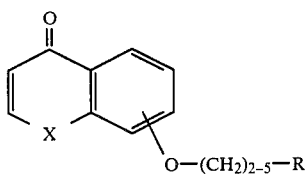

We claim:
1. A compound having the formula

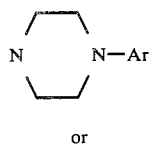

wherein X is oxygen or sulfur; and R is

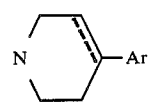

wherein Ar is (a) phenyl, (b) phenyl substituted by lower alkyl, lower alkoxy, lower thioalkoxy, halogen, or trifluoromethyl, or (c) Het wherein Het is 2-, 3-, or 4-pyridinyl or 2-, 3-, or 4-pyridinyl substituted by lower alkyl, lower alkoxy, or halogen; 2-, 4-, or 5-pyrimidinyl or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl or 2- or 3-thienyl substituted by lower alkyl or halogen; 2- or 3-furanyl or 2- or 3-furanyl substituted by lower alkyl or halogen, or 2- or 5-thiazolyl or 2- or 5-thiazolyl substituted by lower alkyl or halogen; and $=$ is a single or double bond; and —O(CH$_2$)$_{2-5}$—R is at the 5, 6, 7, or 8 position of the fused ring system; or pharmacologically acceptable acid addition salts thereof.

2. A compound according to claim 1 wherein X is oxygen.

3. A compound according to claim 1 wherein X is sulfur.

4. A compound according to claim 2 wherein the substituent —O(CH$_2$)$_{2-5}$—R is in the 6 position of the fused ring system.

5. A compound according to claim 2 wherein the substituent —O(CH$_2$)$_{2-5}$—R is in the 7 position of the fused ring system.

6. A compound according to claim 2 wherein —O(CH$_2$)$_{2-5}$—R is —O(CH$_2$)$_3$ or $_4$—R.

7. A compound according to claim 5 wherein the specific embodiment is 7-[3-(4-phenyl-1,2,3,6-tetrahydro-1-pyridyl)propoxy]-4H-1-benzopyran-4-one.

8. A compound according to claim 5 wherein the specific embodiment is 7-[3-(4-phenylpiperazinyl)-propoxy]-4H-1-benzopyran-4-one or the hydrate thereof.

9. A compound according to claim 5 wherein the specific embodiment is 7-[3-(4-(2-pyridyl)piperazinyl)-propoxy]-4H-1-benzopyran-4-one or the hydrochloride salt thereof.

10. A compound according to claim 4 wherein the specific embodiment is 6-[4-(4-phenylpiperazinyl)butoxy]-4H-1-benzopyran-4-one or the hydrochloride salt thereof.

11. A compound according to claim 5 wherein the specific embodiment is 7-[4-(4-phenylpiperazinyl)butoxy]-4H-1-benzo-pyan-4-one or the hydrochloride salt thereof.

12. A compound according to claim 5 wherein the specific embodiment is 7-[3-(4-(3-chlorophenyl-piperazinyl)propoxy]-4H-1-benzo-pyan-4-one, or the hydrochloride salt thereof.

13. A compound according to claim 5 wherein the specific embodiment is 7-[3-(4-(2-methoxyphenyl)-piperazinyl)propoxy]-4H-1-benzopyran-4-one, or the hydrochloride salt thereof.

14. A compound according to claim 5 wherein the specific embodiment is 7-[3-(4-(2-methylphenyl)-piperazinyl)propoxy]-4H-1-benzopyran-4-one, or the hydrochloride salt thereof.

15. A compound according to claim 5 wherein the specific embodiment is 7-[3-(4-(3-methylphenyl)-piperazinyl)propoxy]-4H-1-benzopyran-4-one, or the hydrochloride salt thereof.

16. A compound according to claim 5 wherein the specific embodiment is 7-[3-(4-(4-methylphenyl)-piperazinyl)propoxy]-4H-1-benzopyran-4-one, or the hydrochloride salt thereof.

17. A compound according to claim 5 wherein the specific embodiment is 7-[3-(4-(4-fluorophenyl)-piperazinyl)propoxy]-4H-1-benzopyran-4-one, or the hydrochloride salt thereof.

18. A compound according to claim 5 wherein the specific embodiment is 7-[3-(4-(3,4-dimethylphenyl)-piperazinyl)-propoxy]-4H-1-benzopyran-4-one, or the hydrochloride salt thereof.

19. A compound according to claim 5 wherein the specific embodiment is 7-[3-(2-pyrimidylpiperazinyl)-propoxy]-4H-1-benzopyran-4-one or pharmaceutically acceptable salt thereof.

20. A compound according to claim 6 wherein the specific embodiment is 7-[3-(4-(4-chlorophenyl)-piperazinyl)propoxy]-4H-1-benzopyran-4-one or the hydrate thereof, 7-[3-(4-phenylpiperidinyl)propoxy]-4H-1-benzopyran-4-one or the hydrochloride salt thereof, 7-[3-(4-(2-chlorophenyl)piperazinyl)propoxyl]-4H-1-benzopyran-4-one or the hydrochloride salt thereof; 7-[3-(4-(3,4-dichlorophenyl)piperazinyl)propoxy]-4H-1-benzopyran-4-one or the hydrochloride salt thereof, 7-[3-(4-(4-methoxyphenyl)piperazinyl)propoxy]-4H-1-benzopyran-4-one or the hydrochloride salt thereof, 7-[3-(4-(3-hydroxyphenyl)piperazinyl)propoxy]-4H-1-benzopyran-4-one or the hydrochloride salt thereof, or 5-[3-(4-phenylpiperazinyl)propoxy]-4H-1-benzopyran-4-one.

21. A pharmaceutical composition comprising an antipsychotic effective amount of a compound as claimed in claim 1 with a pharmaceutically acceptable carrier.

22. A method of treating psychosis in a subject suffering therefrom comprising administering to said subject an effective amount of a compound as claimed in claim 1 in unit dosage form.

23. A method according to claim 22 wherein the psychosis is particularly scizophrenia.

* * * * *